(12) United States Patent
Zhu

(10) Patent No.: US 10,436,782 B2
(45) Date of Patent: Oct. 8, 2019

(54) DEVICE FOR IMMUNOCHROMATOGRAPHIC ASSAY

(71) Applicant: Hai Zhu, Shenzhen (CN)

(72) Inventor: Hai Zhu, Shenzhen (CN)

( * ) Notice: Subject to any disclaimer, the term of this patent is extended or adjusted under 35 U.S.C. 154(b) by 192 days.

(21) Appl. No.: 15/325,604

(22) PCT Filed: Oct. 24, 2014

(86) PCT No.: PCT/CN2014/089429
§ 371 (c)(1),
(2) Date: Jan. 11, 2017

(87) PCT Pub. No.: WO2016/061810
PCT Pub. Date: Apr. 28, 2016

(65) Prior Publication Data
US 2017/0153232 A1    Jun. 1, 2017

(51) Int. Cl.
*G01N 33/558* (2006.01)
*B01L 3/00* (2006.01)
*B01L 7/00* (2006.01)

(52) U.S. Cl.
CPC .......... *G01N 33/558* (2013.01); *B01L 3/5023* (2013.01); *B01L 7/00* (2013.01);
(Continued)

(58) Field of Classification Search
CPC ............ G01N 33/558; G01N 33/48714; B01L 3/5023; B01L 2400/0457; B01L 2300/0825; B01L 2300/0672; B01L 2300/044; B01L 2200/026; B01L 7/00; B01L 2200/16; B01L 2400/0644; B01L 2400/0406; B01L 2200/0605; B01L 2200/027; B01L 3/5027; B01L 3/5029; B01L 3/502738;
(Continued)

(56) References Cited

U.S. PATENT DOCUMENTS 6,140,136 A * 10/2000 Lee .................. G01N 33/54366
422/423
6,372,516 B1 * 4/2002 Sun ...................... B01L 3/5023
422/408
(Continued)

FOREIGN PATENT DOCUMENTS

CN          1954203 A      4/2007
CN       201600366 U      10/2010
(Continued)

OTHER PUBLICATIONS

State Intellectual Property Office of the P.R. China (ISR/CN), "International Search Report for PCT/CN2014/089429", China, dated July 15, 2015.

*Primary Examiner* — Lore R Jarrett
(74) *Attorney, Agent, or Firm* — Locke Lord LLP; Tim Tingkang Xia, Esq.

(57) ABSTRACT

A device for immunochromatographic assay includes a housing and a vessel body. The housing has an upwardly-extending hollow protrusion for housing the vessel body. The vessel body has a vessel body wall and a vessel body bottom. A raised tip and a fence surrounding the tip are arranged in the housing. The vessel body and the raised tip can be moved towards each other such that the raised tip can break the vessel body bottom to release liquid in the vessel body.

4 Claims, 6 Drawing Sheets

(52) U.S. Cl.
CPC ..... *B01L 2200/026* (2013.01); *B01L 2200/16* (2013.01); *B01L 2300/044* (2013.01); *B01L 2300/0672* (2013.01); *B01L 2300/0825* (2013.01); *B01L 2400/0457* (2013.01)

(58) Field of Classification Search
CPC ..... B01L 2400/0683; B01L 2400/0655; B01L 2400/0638; B01L 2300/0887; B01L 2300/0867; B01L 3/5085; B01L 3/50273; A61B 10/0045; A61B 2010/0077; A61B 2010/0074; A61B 10/007; A61B 10/0051; Y10T 137/218
See application file for complete search history.

(56) References Cited

U.S. PATENT DOCUMENTS

| | | | |
|---|---|---|---|
| 2003/0175993 A1* | 9/2003 | Toranto | G01N 33/487 436/518 |
| 2005/0119589 A1* | 6/2005 | Tung | A61B 10/0045 600/584 |
| 2005/0272169 A1* | 12/2005 | Griffin | B01L 3/502738 436/514 |
| 2011/0236879 A1 | 9/2011 | Egan et al. | |

FOREIGN PATENT DOCUMENTS

| | | |
|---|---|---|
| CN | 102998446 A | 3/2013 |
| CN | 203178275 U | 9/2013 |
| EP | 2713164 A1 | 4/2014 |

* cited by examiner

DEVICE FOR IMMUNOCHROMATOGRAPHIC ASSAY

CROSS-REFERENCE TO RELATED APPLICATIONS

This application is a U.S. national phase application of PCT Patent Application Serial No. PCT/CN2014/089429, filed on Oct. 24, 2014, which is hereby incorporated herein by reference in its entirety.

TECHNICAL FIELD

The present application belongs to the technical field of immunochromatographic assay, and relates to a device for immunochromatographic assay.

BACKGROUND ART

Immunochromatography is a rapid detection/diagnosis technique, and is typically classified into sandwich and competitive immunochromatographic assays. The mechanism for sandwich immunoassay is as follows: a specific antibody is firstly immobilized to a zone (line) of a nitrocellulose membrane and the like (i.e., a chromatographic membrane) in a test paper; after one end of a sample pad in the test paper is immersed in a liquid sample (e.g., urine, serum, milk, etc.) or alternatively the liquid sample is added to one end of the sample pad, the sample moves towards the other end along the nitrocellulose membrane under capillary action; when the sample moves to the zone (line) immobilized with the antibody, a corresponding antigen in the sample will specifically bind to the antibody; and then this zone may develop a certain color or emit fluorescence by means of immunocolloidal gold technique, immunoenzymatic staining or immunofluorescence technique, thereby achieving specific immunological diagnosis and detection. On the other hand, the mechanism for competitive immunochromatographic assay, which is used for detecting small molecules, can be described briefly in two cases as follows: when a small molecule conjugate is immobilized to the nitrocellulose membrane, the binding of a small molecule to be detected to a free antibody makes it impossible for the free antibody to bind to the small molecule conjugate on the nitrocellulose membrane, that is, the small molecule to be detected competes with the small molecule conjugate on the nitrocellulose membrane for opportunity to bind to the free antibody; and when a specific antibody is immobilized to the nitrocellulose membrane, the small molecule to be detected competes with the free labeled small molecule for opportunity to bind to the specific antibody immobilized to a specific zone of the nitrocellulose membrane. Then, the presence or absence of the analyte is determined according to decreased or disappeared color or fluorescence of the zone to which the small molecule conjugate or the specific antibody is immobilized.

During the above detection, the color or fluorescence is observed or evaluated with the naked eye or a detection instrument in qualitative, semi-quantitative and quantitative manners. At present, the immunochromatographic technique and such technique-based test paper products have been widely applied in the fields such as medical detection and food safety inspection.

Traditional immunochromatographic test strips made on the basis of this technique typically comprise the following components: a backing and a sample pad attached to the backing, a conjugate pad (the conjugate pad for label), a cellulose membrane, an absorbent pad, and the like. When detection is carried out, once a sample is added drop-wise onto the sample pad, the sample migrates on a chromatographic strip in the sample pad under capillary action. During the migration, the sample reacts specifically with a label on the conjugate pad to produce an immunocomplex; and the immunocomplex continues to migrate and specifically binds to the corresponding antigen/antibody in the detection region of the cellulose membrane to form a visible or detectable band.

The above-mentioned immunochromatographic test strips in traditional reaction mode usually have the following technical drawbacks:

(1) During the drying of the conjugate pad which is produced by means of immersion or spraying, owing to the action of "edge effect", the reagents such as labels on the conjugate pad are rendered unevenly distributed.

(2) When a sample flows through the sample pad and the conjugate pad, there is random error to a certain degree for the amount of the reagents which are released from the conjugate pad and participate in the reaction, due to the randomness of the flow pattern and of flow-through time of the liquid, in particular when there is a snap.

(3) The change in the ambient temperature has some influences on the reaction.

(4) The immunochromatographic test strips in traditional reaction mode is generally in a form having a snap, and thus it is inconvenient to stop reaction by a way of removing the sample pad, and it is prone to cause the results to have a relatively large error, due to the difference in reaction time when observed.

(5) When the results are evaluated with the naked eye, difference may occur due to the different environmental lighting, personal vision, and personal evaluation criteria.

The above technical drawbacks lead to or exacerbate error of results, especially when such technique is used for quantitative and semi-quantitative detection.

At present, there are improved immunochromatographic test strips which have been developed to overcome the above drawbacks, for example, the test strips in "reaction vessel (micropore)+test strip" mode, which do not comprise the sample pad/conjugate pad. The improved immunochromatographic test strips have relatively more advantages over the test strips in traditional reaction mode, but they still have drawbacks including excessive operation steps and troublesome application. Typically, a single detection comprises the following 5 steps: 1. adding a sample into the reaction vessel and mixing it homogenously; 2. incubating the reaction vessel for a period of time; 3. inserting the test strip into the reaction vessel and allowing for reaction in the incubator for a period of time; 4. taking out the test strip, and removing the sample pad, thereby stopping the reaction; and 5. placing the test strip in a reader to read the results. Such cumbersome operation steps are disadvantageous to rapid on-site detection in terms of efficiency and simplicity, which is obvious especially for clinical detection. Therefore, there is a need to provide a device capable of performing a rapid immunochromatographic assay.

SUMMARY OF THE INVENTION

The present application aims at providing a device for immunochromatographic assay and solving the problems associated with cumbersome detection steps and long detection period existing in the prior art.

The Solutions to the Problems

The Technical Solutions

An embodiment of the present application provides a device for immunochromatographic assay, comprising a housing and a vessel body located inside the housing, wherein, the housing comprises an upwardly extending hollow protrusion for housing the vessel body, the vessel body comprises a vessel body wall and a vessel body bottom, the housing is provided with a raised tip under the vessel body bottom, the vessel body and the raised tip are capable of moving towards each other, and during the movement, the raised tip can break the vessel body bottom to release a liquid contained in the vessel body; and the housing is further provided with a fence under the vessel body bottom, the fence comprises an annular structure corresponding to an outer circumference of the vessel body bottom, and a groove communicating with the annular structure.

Another embodiment of the present application provides a device for immunochromatographic assay, wherein the fence is provided at a place where the annular structure communicates with the groove with a projection, which is used together with the groove for fixing a test strip.

Another embodiment of the present application also provides a device for immunochromatographic assay, wherein a portion of a bottom of the housing inside the annular structure of the fence is a ramp structure, and a base of the ramp structure is located at the place where the annular structure communicates with the groove.

Another embodiment of the present application also provides a device for immunochromatographic assay, wherein the hollow protrusion is connected to the vessel body via screw threads.

Another embodiment of the present application also provides a device for immunochromatographic assay, wherein the vessel body wall is provided at an upper end of an outer surface with at least two outwardly extending protruding parts, through which a torsional force can be applied to the vessel body, such that the vessel body moves towards the raised tip in the housing, and therefore the raised tip breaks the vessel body bottom to release the liquid in the vessel body.

Another embodiment of the present application provides a device for immunochromatographic assay, wherein the hollow protrusion is connected with the vessel body inside the hollow protrusion via guide rails and chutes, wherein at least two chutes are provided on an inner surface of the hollow protrusion, and guide rails corresponding to the chutes are provided on an outer surface of the vessel body. A downward pressure may be applied to the vessel body, such that the vessel body moves towards the raised tip along the guide rails, and thereby the vessel body bottom is broken and the liquid in the vessel body is released.

Another embodiment of the present application also provides a device for immunochromatographic assay, wherein the vessel body is connected to the hollow protrusion via at least two snaps located on an outer surface of the vessel body bottom.

Another embodiment of the present application also provides a device for immunochromatographic assay, wherein the housing comprises a top housing, a bottom housing and a housing-pressing plate, wherein the hollow protrusion is located on the top housing, the fence is located on the bottom housing, the raised tip is located on the housing-pressing plate, and a hole corresponding to the raised tip is provided inside the annular structure of the fence. A joint between the raised tip and the hole prevents from liquid leakage when the raised tip passes through the hole and breaks the vessel body bottom.

Another embodiment of the present application also provides a device for immunochromatographic assay, wherein the bottom housing is connected to the housing-pressing plate via a supporting pin, and the housing-pressing plate is capable of pivoting on the supporting pin, thereby causing the raised tip to break the vessel body bottom and release the liquid in the vessel body.

Beneficial Effect of the Invention

During the use of the device for immunochromatographic assay provided by the present application, the detection process of the prior "reaction vessel (micropore)+test strip mode", which otherwise requires five steps for implementation, can be automatically performed with supporting detection instruments only by adding a sample to the reaction vessel and mixing the sample, thereby shortening the detection time. In the meantime, upon confirmation by the comparative embodiments, it can be seen that the device for immunochromatographic assay of the present application can bring about a detection effect of the same sensitivity as that of the detection means in the prior art. Consequently, the device for immunochromatographic assay of the present application retains all advantages of the conventional detection mode while avoiding drawbacks of the latter such as excessive operation steps and troublesome application.

DETAILED DESCRIPTION OF THE INVENTION

Figure 1:
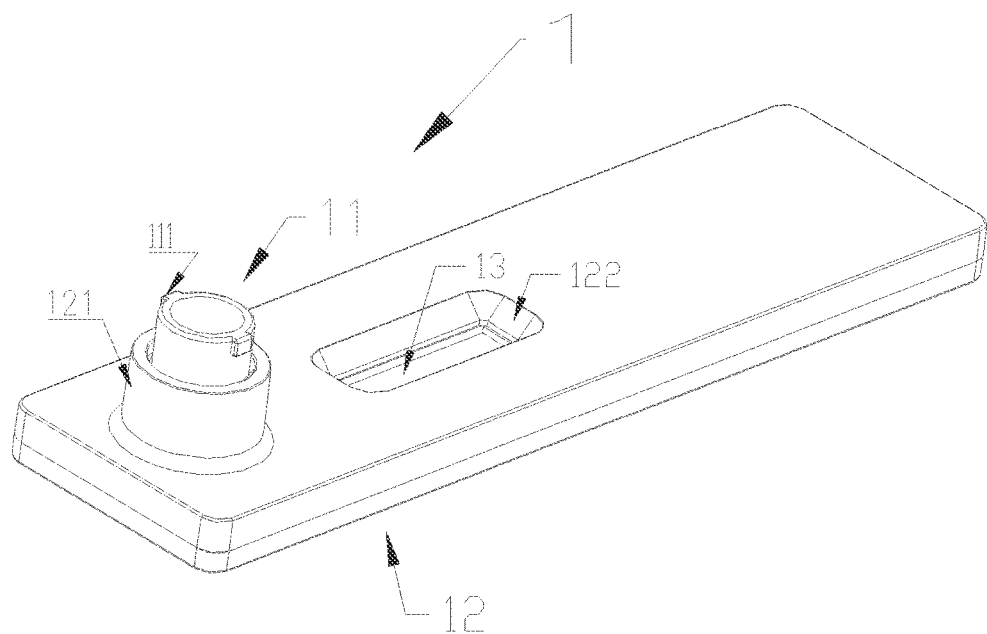
FIG. 1 shows a perspective view of a device for immunochromatographic assay according to one embodiment of the present application.

Below, the present application is further illustrated in detail in conjunction with the drawings and the embodiments in order to more clearly describe the technical problem to be solved by the present application, the technical solutions and the beneficial effects. It should be understood that the specific embodiments described herein are only for the purpose of explaining the present application and are not intended to limit the scope of the present application.

An embodiment of the present application provides a device for immunochromatographic assay comprising a housing and a vessel body located inside the housing. The housing comprises an upwardly extending hollow protrusion for housing the vessel body. The vessel body, which is separable from the housing, comprises a vessel body wall and a vessel body bottom, and may contain a liquid reagent or a powder reagent, to which a liquid sample may be added during detection. The housing is provided under the vessel body bottom with a raised tip and a fence surrounding the raised tip, wherein the raised tip may or may not contact with the vessel body bottom. The raised tip and the vessel body may move towards each other, and by such movement, the raised tip penetrates the vessel body bottom and meanwhile the liquid contained in the vessel body is released. At this time the liquid contained in the vessel body will be completely released. The fence surrounding the raised tip comprises an annular structure corresponding to an outer circumference of the vessel body bottom and a groove communicating with the annular structure, wherein the annular structure is used for receiving the liquid released from the vessel body and allowing the liquid in contact with the test strip, and the groove communicating with the annular structure is used for placing the test strip for detection.

By utilizing the device of the present application, mixing and reaction of a liquid can be performed in the vessel body, and then the raised tip breaks the vessel body bottom to release the liquid in the vessel body, allowing all the liquid to flow into the fence under the vessel body. The fence receives all the liquid, which contacts with one end of the test strip and moves towards the other end of the test strip under the capillary action. In such way, the detection is completed. Compared with the traditional multi-step detection method, the present detection method does not include the sample application step, shortens the detection time and increases the detection efficiency.

In a preferred embodiment, in the device for immunochromatographic assay of the present application, the fence is provided at a place where the annular structure communicates with the groove with a projection, which is used together with the groove for fixing a test strip, thereby making the test strip located in the groove tightly.

Preferably, in the device for immunochromatographic assay of the present application, a portion of a bottom of the housing inside the annular structure of the fence is a ramp structure, and a base of the ramp structure is located at the place where the annular structure communicates with the groove. As one end of the test strip is located at the base of the ramp structure, the liquid flowed downwards from the vessel body all is allowed to flow towards the test strip.

The device for immunochromatographic assay of the present application further comprises an observation window in the housing.

The device for immunochromatographic assay of the present application may employ a variety of means to move the raised tip and the vessel body towards each other. According to one embodiment, the raised tip is fixed in the housing and the vessel body is allowed to move towards the raised tip, thereby breaking the vessel body bottom to release the liquid. The vessel body may be connected to the hollow protrusion via screw threads, and the movement towards each other may be performed via the screw threads. In this case, the vessel body is provided on an upper end of an outer surface with two or more protruding parts, through such protruding parts an external force may be applied to the vessel body by means of an external device such that the vessel body rotates. In this way, the vessel body moves towards the raised tip along the screw threads, and the vessel body bottom is broken by the raised tip. In this embodiment, the fence is provided with a positioning rib, which is used for limiting a distance that the vessel body moves downwards.

According to another embodiment, the vessel body may be connected to the hollow protrusion via guide rails and chutes. For example, the vessel body may be provided on an outer surface with two or more protruding guide rails, the hollow protrusion may be provided on an inner surface with the corresponding number of chutes corresponding to the protruding guide rails, and the protruding guide rails are movable in the chutes. A downward pressure may be applied to the vessel body by means of an external device, such that the vessel body moves towards the raised tip along the chutes and the raised tip breaks the vessel body bottom.

Prior to penetration of the vessel body bottom, an external device may be used for timing so as to allow the liquid in the vessel body to react completely. Then, a torsional force or a pressure is applied to the vessel body so as to allow the raised tip to break the vessel body bottom, thereby releasing the liquid in the vessel body.

According to another embodiment of the present application, the vessel body and the hollow projection are immovable relative to each other, and the raised tip is allowed to move towards the vessel body and break the vessel body bottom during detection. This technical solution can be performed by additionally providing a housing-pressing plate. In this case, the housing of the device comprises a top housing, a bottom housing and a housing-pressing plate, wherein the hollow protrusion is located on the top housing, the fence is located in the bottom housing, and the raised tip is located on the housing-pressing plate; and a hole corresponding to the raised tip is provided inside the annular structure of the fence. The housing-pressing plate is connected with the bottom housing via two supporting pins (short rods) located in the concavity, whereby the housing-pressing plate can pivot on the supporting pins, and the movement of the raised tip can be achieved by applying a pressure to the other end of the housing-pressing plate opposite to the raised tip. A portion of a bottom surrounded by the annular structure of the bottom housing is provided with a hole corresponding to the raised tip, and the liquid leakage between the raised tip and the hole can be prevented when the raised tip passes through the hole and breaks the vessel body bottom to release the liquid. That is, the liquid flowed out from the vessel body is completely kept in the fence and does not permeate into components under the fence, which renders the detection more accurate.

The present application is further illustrated by the following specific embodiments.

Figure 2:
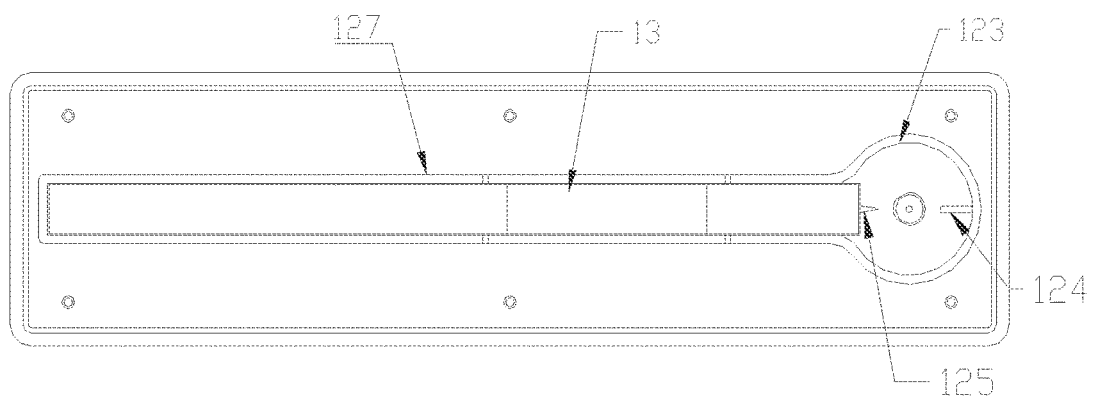
FIG. 2 shows a top view of the bottom housing part of a device for immunochromatographic assay according to one embodiment of the present application.
Figure 3:
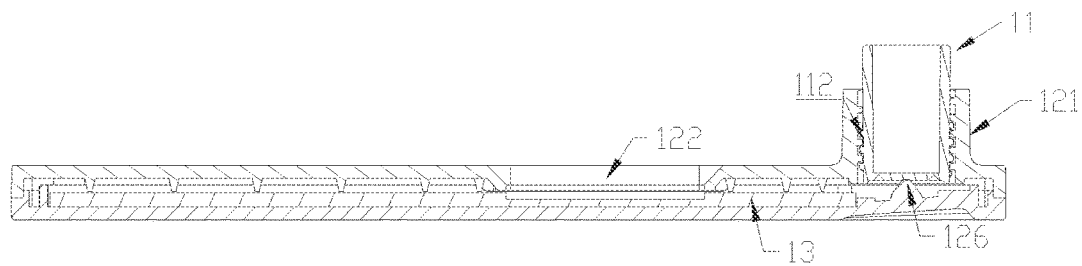
FIG. 3 shows a section view of a device for immunochromatographic assay according to one embodiment of the present application.
Figure 4:
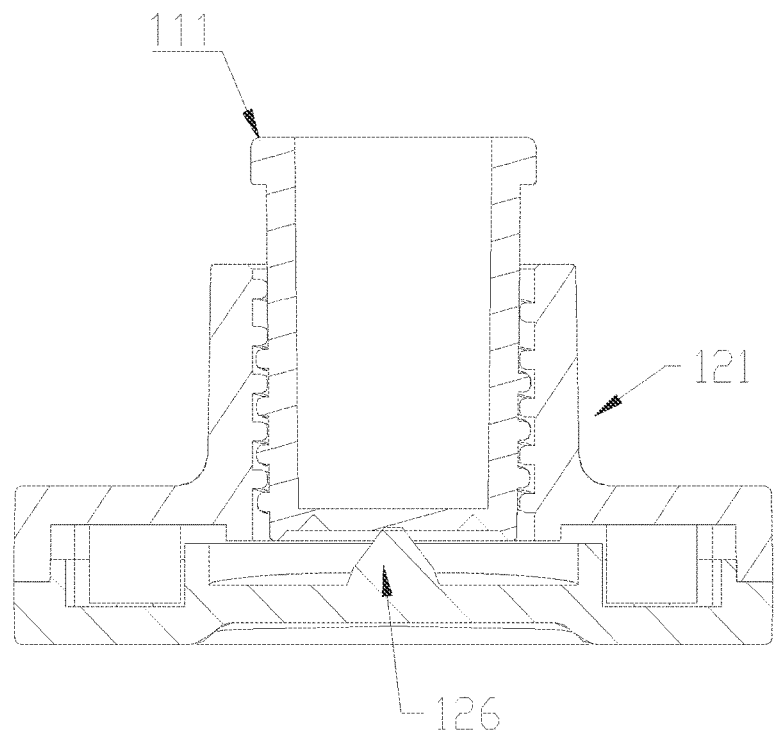
FIG. 4 shows a section view of the hollow protrusion part of a device for immunochromatographic assay according to one embodiment of the present application.
Figure 5:
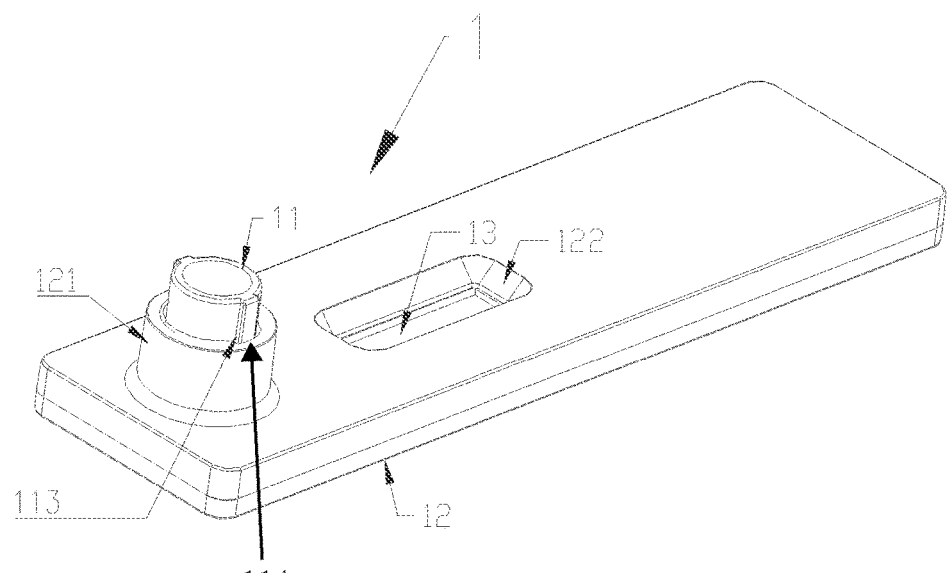
FIG. 5 shows a perspective view of a device for immunochromatographic assay according to another embodiment of the present application.
Figure 9:
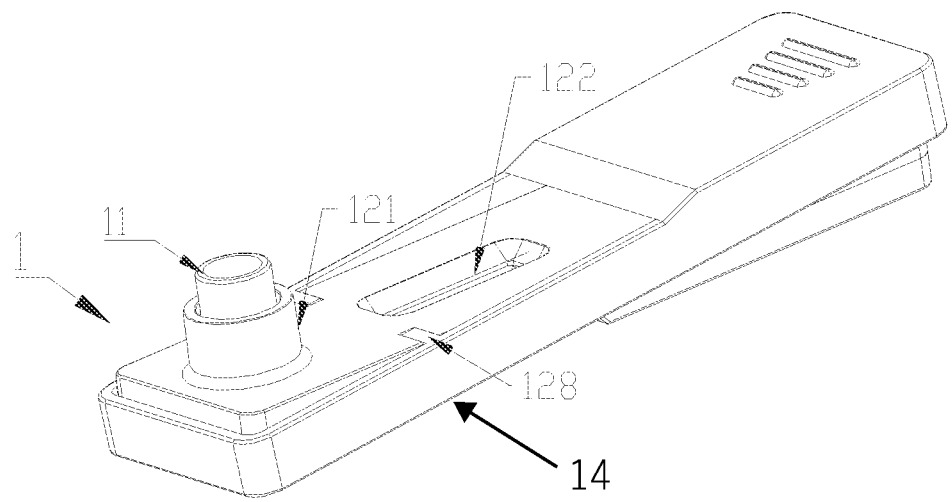
FIG. 9 shows a perspective view of a device for immunochromatographic assay according to another embodiment of the present application.

As shown in FIGS. 1, 5 and 9, the present application provides a device 1 for immunochromatographic assay, comprising a vessel body 11 and a housing 12, wherein the housing 12 comprises an upwardly extending hollow protrusion 121 which is used for housing the vessel body 11, and an observation window 122. A test strip 13 is located in the housing 12, and can be observed from the observation window 122. In the embodiments as shown in FIGS. 1-4, the vessel body 11 and the hollow protrusion 121 of the housing 12 are connected via screw threads. As shown in FIG. 1, the vessel body 11 comprises two protruding parts 111. There may be two or more protruding parts 111. A torsional force may be applied through the protruding parts 111 to the vessel body 11 by means of an external device, causing the vessel body 11 to move towards the raised tip by the screw threads. The housing 12 may comprise two portions, i.e., a top housing and a bottom housing. FIG. 1 shows a structure in which the top housing and the bottom housing are engaged together. FIG. 2 shows the structure of the bottom housing which comprises an annular structure 123 and a groove 127 communicating with the annular structure 123. The annular structure 123 is provided with a positioning rib 124 and a projection 125 therein, wherein the projection 125 is located at a place where the annular structure 123 communicates with the groove 127. The test strip 13 is placed in the groove 127, and is positioned by the groove 127 and the projection 125. The positioning rib 124 may limit the movement distance of the vessel body 11 so as to retain a sufficient space in the annular structure 123 to contain the reaction liquid. FIG. 3 shows a section view of the device 1 for immunochromatographic assay in the longitudinal direction of the test strip 13, and FIG. 4 shows a schematic section view of a connection portion between the hollow protrusion 121 and the vessel body 11. The vessel body 11 comprises on an upper end of an outer surface two protruding parts 111, and the housing 12 is provided under the vessel body 11 with a raised tip 126. A torsional force may be applied to the two protruding parts 111 on the upper end of the outer surface of the vessel body 11, such that with the screw threads the vessel body 11 moves towards the raised tip 126 relative to the hollow protrusion 121 of the housing 12, and the raised tip 126 breaks the vessel body bottom of the vessel body 11 to release the liquid from the vessel body 11.

Figure 6:
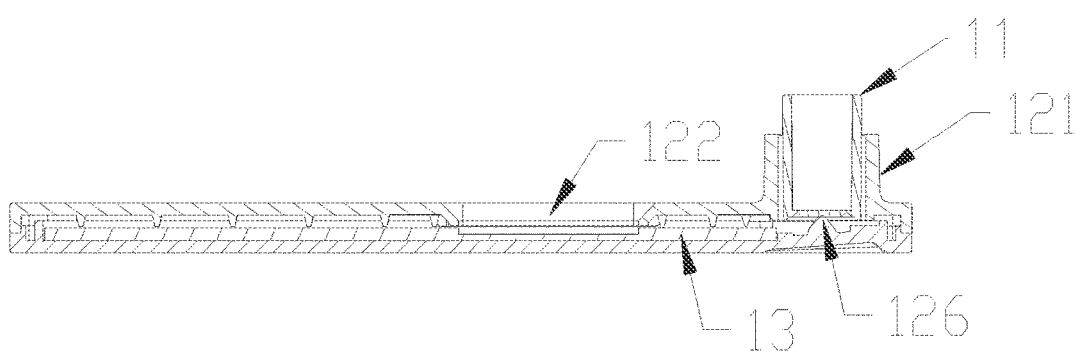
FIG. 6 shows a section view of a device for immunochromatographic assay according to another embodiment of the present application.
Figure 7:
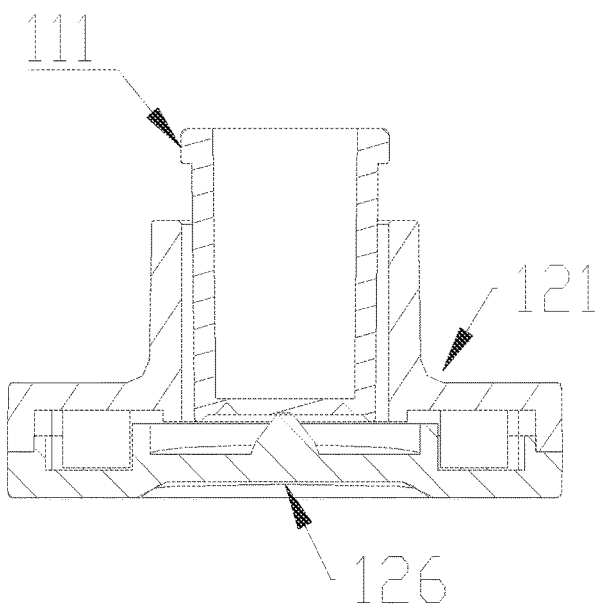
FIG. 7 shows a section view of the hollow protrusion part of a device for immunochromatographic assay according to another embodiment of the present application.

FIGS. 5-7 show another embodiment of the device of the present application. In this embodiment, the vessel body 11 is provided on the outer surface with protruding guide rails 113, and the hollow protrusion 121 of the housing 12 is correspondingly provided with chutes 114, wherein the protruding guide rails 113 are respectively located in the chutes 114, and the guide rails 113 and the chutes 114 each may be two or more in number. In the present embodiment, it is schematically shown that the vessel body 11 is provided with two guide rails 113. The vessel body 11 can be moved downwards along the chutes 114 in the hollow protrusion 121 by applying a pressure to the vessel body 11, such that the vessel body bottom of the vessel body 11 is broken with the raised tip 126 in the housing 12 and the liquid is released from the vessel body 11. The liquid all flows into the annular structure 123 and comes into contact with the test strip 13, thereby performing the detection.

Figure 8:
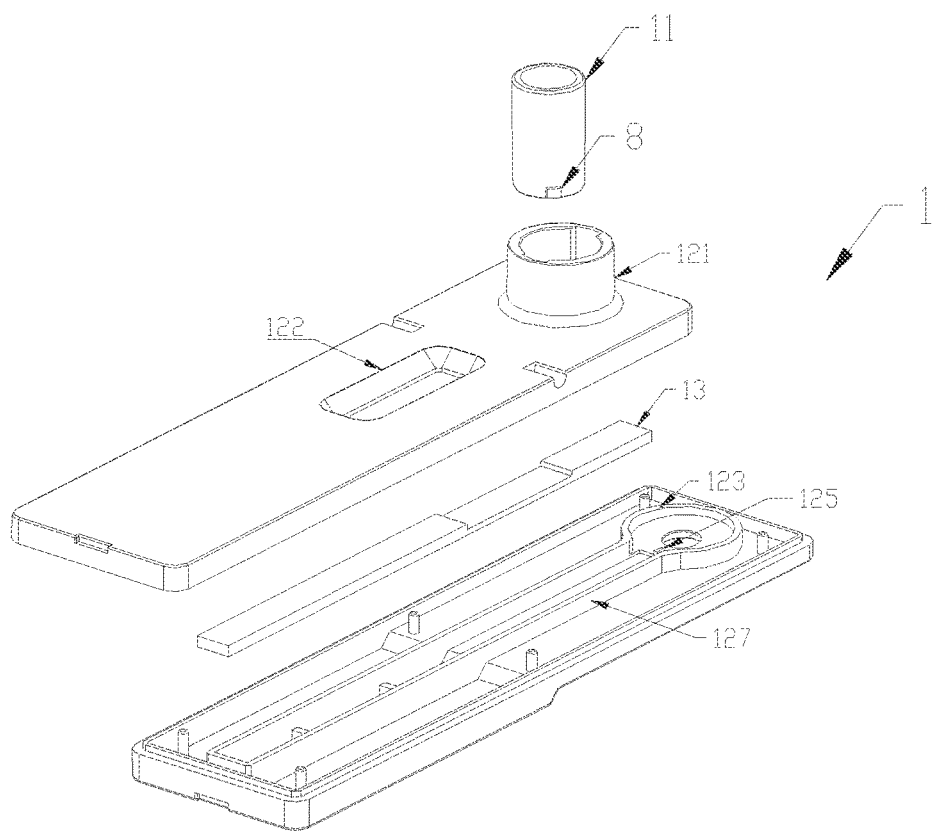
FIG. 8 shows an exploded view of a device for immunochromatographic assay according to another embodiment of the present application.
Figure 10:
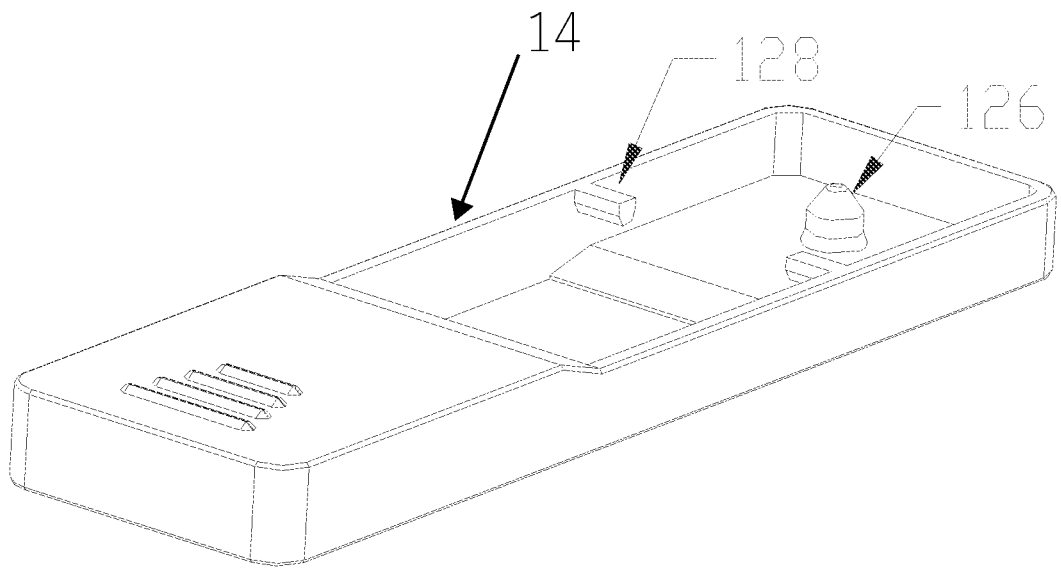
FIG. 10 shows a perspective view of a housing-pressing plate of a device for immunochromatographic assay according to another embodiment of the present application.
Figure 11:
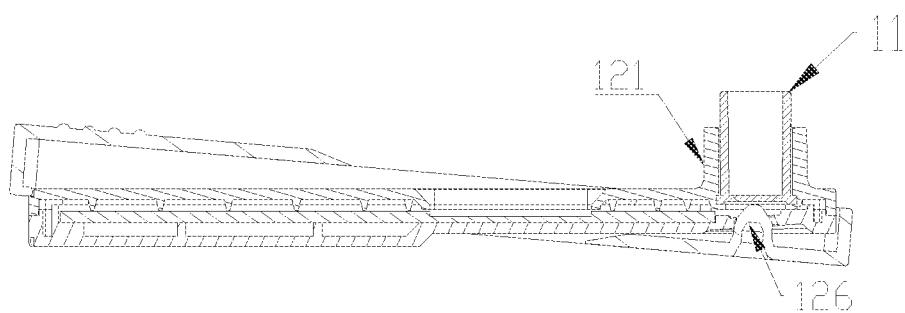
FIG. 11 shows a section view of a device for immunochromatographic assay according to another embodiment of the present application.

FIGS. 8-11 show another embodiment of the device of the present application. In this embodiment, the housing 12 further comprises a housing-pressing plate 14 disposed outside the bottom housing, as shown in FIG. 9. As shown in FIGS. 8 and 10, the hollow protrusion 121 is located in the top housing, the annular structure 123 is located in the bottom housing and is provided in an area of the bottom housing surrounded by the annular structure 123 with a hole corresponding to the raised tip 126, and the raised tip 126 is located in the housing-pressing plate 14. As shown in FIG. 8, the vessel body 11 is provided on an outer surface of the vessel body bottom with two snaps 8, which are used for making the vessel body 11 and the hollow protrusion 121 fixed relative to each other. In this embodiment, the raised tip 126 moves towards the vessel body 11 and breaks the vessel body bottom of the vessel body 11. As shown in FIGS. 9-11, the housing-pressing plate 14 comprises two supporting pins 128, and the bottom housing is correspondingly provided with two concavities, with the supporting pins 128 located in the concavities, whereby the housing-pressing plate 14 and the bottom housing are fixed relative to each other. The housing-pressing plate 14 can pivot on the supporting pins 128 such that the raised tip 126 can move towards the vessel body 11 and break the vessel body bottom, thereby releasing the liquid in the vessel body. In order to increase the frictional force, the supporting pins may be provided at a force-bearing end with an anti-slip strip, as shown in FIGS. 9 and 10.

In the case of using the device for detection according to the present application shown in FIGS. 1-4, the detection can be carried out according to the following steps:

(1) A freeze-dried detection reagent or a liquid detection reagent is placed in the vessel body 11 in advance.

(2) When a sample is detected, a liquid sample is added into the vessel body 11 and mixed homogenously; and at the same time, a supporting detection instrument is used to control the reaction time and provide a desired reaction temperature.

(3) After the reaction of the sample is completed, the vessel body 11 is rotated 180° by the supporting detection instrument via the protruding parts 111 provided on the vessel body 11, such that the raised tip 126 in the housing 12 penetrates the vessel body bottom of the vessel body 11, which allows the reacted liquid to be released into the annular structure 123 and to permeate towards the test strip, thereby effecting the reaction with the test strip. During this procedure, the supporting detection instrument still provides the desired reaction temperature.

(4) Immediately after the reaction between the reacted liquid and the test strip is completed, the supporting detection instrument reads the reaction results.

In the case of using the device for detection shown in FIGS. 8-11, the steps are the same as the above except for step (3), wherein an external force is applied to one end of the housing-pressing plate 14, such that the raised tip 126 at the other end of the housing-pressing plate 14 moves upwards and penetrates the vessel body bottom of the vessel body 11.

In the case of using the device for detection shown in FIGS. 8-11, the steps are the same as the above except for step (3), wherein an external force is applied to one end of the housing-pressing plate, such that the raised tip 126 at the other end of the housing-pressing plate moves upwards and penetrates the vessel body bottom of the vessel body 11.

Quantitative, semi-quantitative or qualitative results can be obtained by the above procedures.

The housing of the device of the present application may be provided with a barcode, a two-dimensional code or the like, from which relevant information can be read by a supporting detection instrument. The information from the barcode or two-dimensional code etc., may include test items, corrected parameters of detected results of products for test cards in this lot, and information based on anti-counterfeiting or for associating a supporting detection instrument with a test card, but is not limited to the above-described information.

In the present application, both the device of the present application and the traditional detection device were used to detect the milk (raw milk) for chloramphenicol residues, and were compared in terms of detection period, sensitivity, precision and accuracy. The detection involves three groups:

Group A: the device for detection of the present application

Group B: naked strip+reaction vessel group

Group C: the traditional snap group

The detection results are as follows:

1. The Following Table Shows the Comparative Results of Detection Period.

TABLE 1

| comparison of detection period | | |
|---|---|---|
| Group | Reaction condition | Detection period |
| Group A | 40° C. | 3 min + 3 min |
| Group B | 40° C. | 3 min + 5 min |
| Group C | room temperature | 10 min |

2. Comparative Results of Detection Sensitivity and Precision

A known negative milk sample was used for analyte addition, in which the analyte was added in 5 gradients, i.e., 0.00 ppb, 0.05 ppb, 0.10 ppb, 0.15 ppb and 0.2 ppb. The experiments were repeated 20 times for each of the gradients, and the results were evaluated by observation with the naked eye and an instrument, respectively.

The results showed (data not shown) that 100% detection was achieved with the three groups of detection devices, namely Groups A, B, and C, when 0.1 ppb of the analyte was added.

3. Accuracy Experiments

50 Samples which had been confirmed by LC-MS were detected with the above three different groups of detection devices for evaluating the consistency between the results detected by the three detection methods and the results obtained by LC-MS.

The detection results showed that the results in Group A were 100% consistent with the results of LC-MS, Group B was 100% consistent, and Group C was 98% consistent.

From the above detection results, it can be seen that the detection device of the present application is consistent with the traditional method in terms of sensitivity, precision and accuracy while remarkably shortening the detection period as compared with the prior method.

The foregoing examples are only preferred embodiments of the present application and are not intended to limit the present application. Any modifications, equivalent substitutions, and improvements made within the spirit and the principles of the present application shall be encompassed by the scope of the present application.

What is claimed is:

1. A device for immunochromatographic assay, comprising a housing and a vessel body located inside the housing, wherein, the housing comprises an upwardly extending hollow protrusion for housing the vessel body, the vessel body comprises a vessel body wall and a vessel body bottom, the housing is provided under the vessel body bottom with a raised tip, the vessel body and the raised tip are capable of moving towards each other, and during the movement, the raised tip can break the vessel body bottom to release a liquid contained in the vessel body;

the housing is further provided with a fence surrounding the raised tip at a bottom of the housing, the fence comprises an annular structure corresponding to an outer circumference of the vessel body bottom, and a groove communicating with the annular structure;

the fence is provided at a place where the annular structure communicates with the groove with a projection, which is used together with the groove for fixing a test strip;

a portion of a bottom of the housing inside the annular structure of the fence is a ramp structure, and a base of the ramp structure is located at the place where the annular structure communicates with the groove;

the vessel body is connected to the hollow protrusion via at least two snaps located on an outer surface of the vessel body bottom;

the housing comprises a top housing, a bottom housing and a housing-pressing plate, wherein the hollow protrusion is located on the top housing, the fence is located on the bottom housing, the raised tip is located on the housing-pressing plate, and a hole corresponding to the raised tip is provided inside the annular structure of the fence; and the bottom housing is connected to the housing-pressing plate via a supporting pin, and the housing-pressing plate is capable of pivoting on the supporting pin, thereby causing the raised tip to break the vessel body bottom.

2. The device for immunochromatographic assay according to claim 1, wherein, the hollow protrusion is connected to the vessel body via screw threads.

3. The device for immunochromatographic assay according to claim 2, wherein, the vessel body wall is provided at an upper end of an outer surface with at least two outwardly extending protruding parts, through which a torsional force can be applied to the vessel body.

4. The device for immunochromatographic assay according to claim 3, wherein, the hollow protrusion is connected with the vessel body via guide rails and chutes, wherein at least two chutes are provided on an inner surface of the hollow protrusion, and guide rails corresponding to the chutes are provided on an outer surface of the vessel body.

* * * * *